United States Patent [19]

Mayes

[11] Patent Number: 4,709,810

[45] Date of Patent: Dec. 1, 1987

[54] CONTAINER FOR AN ELECTROPHORETIC SUPPORT MEDIUM

[75] Inventor: David G. Mayes, Beaumont, Tex.

[73] Assignee: Helena Laboratories Corporation, Beaumont, Tex.

[21] Appl. No.: 930,620

[22] Filed: Nov. 14, 1986

[51] Int. Cl.[4] ............................................. G01N 27/28
[52] U.S. Cl. ................................ 206/205; 204/182.8; 204/299 R
[58] Field of Search ............... 206/461, 464, 470, 471, 206/205; 156/295, 308.6; 204/182.8, 299 R

[56] References Cited

U.S. PATENT DOCUMENTS

| | | |
|---|---|---|
| 2,874,091 | 2/1959 | Fisk . |
| 3,337,416 | 8/1967 | Forgacs . |
| 3,407,133 | 10/1968 | Oliva et al. ...................... 204/299 R |
| 3,479,265 | 11/1969 | Elevitch ...................... 204/299 R X |
| 3,482,943 | 12/1969 | Csizmas et al. . |
| 3,523,863 | 8/1970 | Juhos . |
| 3,615,006 | 10/1971 | Freed . |
| 3,622,484 | 11/1971 | Cawley . |
| 3,635,808 | 1/1972 | Elevitch . |
| 3,695,424 | 10/1972 | Cristy et al. . |
| 3,710,975 | 1/1973 | Jansen . |
| 3,725,004 | 4/1973 | Johnson et al. . |
| 3,756,393 | 9/1973 | Markwitz et al. . |
| 3,767,560 | 10/1973 | Elevitch . |
| 3,803,020 | 4/1974 | Stephen . |
| 3,856,656 | 12/1974 | Brink ............................ 204/182.8 X |
| 3,873,433 | 3/1975 | Seidel et al. . |
| 3,875,045 | 4/1975 | Bergraham et al. ......... 204/182.8 X |
| 3,888,759 | 6/1975 | Elson et al. . |
| 4,011,350 | 3/1977 | Markovits . |
| 4,077,515 | 3/1978 | Shoberg . |
| 4,314,897 | 2/1982 | Monte et al. ................. 204/182.8 X |
| 4,619,364 | 10/1986 | Czopor, Jr. ..................... 206/461 X |

Primary Examiner—Stephen Marcus
Attorney, Agent, or Firm—Cullen, Sloman, Cantor, Graver, Scott & Rutherford

[57] ABSTRACT

A container for protecting and enclosing an electrophoretic support medium. The container includes a top portion and a bottom portion, which when closed sealingly engage one another. The bottom portion has a recess formed therein for accommodating the support medium and at least a portion of the recess has a substantially smooth planar surface. A liquid disposed between and in contact with the planar surface of the bottom portion and the support medium provides sufficient contact adhesion to securely retain the support medium within the recess.

18 Claims, 5 Drawing Figures

CONTAINER FOR AN ELECTROPHORETIC SUPPORT MEDIUM

FIELD OF THE INVENTION

The present invention relates generally to electrophoresis and particularly to a container for storing and protecting an electrophoretic support medium contained therein.

BACKGROUND OF THE INVENTION

It is known that an analysis of ionizable compounds, such as proteins, can be made by subjecting a sample, of for example blood, to an electrical potential as taught in U.S. Pat. Nos. 3,407,133 (Oliva et al.) and 3,479,265 (Elevitch).

The sample to be analyzed by electrophoresis is placed on a suitable support medium, such as a gel, of the types disclosed in U.S. Pat. No. 3,725,004 (Johnson et al.). Such support medium may include, for example; (1) aqueous solutions of agar or agarose as disclosed in U.S. Pat. Nos. 3,281,409 (Blethen), 3,335,127 (Polson), 3,362,884 (Morse) and 3,766,047 (Elevitch); (2) synthetic polymeric gelling agents as disclosed in U.S. Pat. No. 3,046,201 (White et al.); and (3) cellulose and cellulose acetate as disclosed in U.S. Pat. No. 3,360,440 (Haab et al.). However, such support mediums are prone to dehydration, thus, requiring air tight enclosure by containers to completely prevent evaporation of the water from the support medium as disclosed in U.S. Pat. Nos. 3,875,045 (Bergrahm et al.) and 4,314,897 (Monte et al.). This has been accomplished by providing adhesive sealing strips to the containers, or the use of moistened pads within the containers as disclosed in U.S. Pat. No. 3,856,656 (Brink). Also, such containers have been completely enclosed within air tight bags. Dehydration is undesirable because it affects the shelf life of the support medium and causes variations in the migration of the ionizable compounds during use. In addition to requiring air tight enclosure, such containers have required secure retention of the support medium within the container to prevent the support medium from coming in contact with any part of the container to prevent flaws, such as marks or cracks in the support medium. Such flaws are aggravated by shrinkage of the support medium caused by dehydration as disclosed, for example, in U.S. Pat. No. 4,314,897 (Monte et al.).

SUMMARY OF THE INVENTION

In contrast to the prior art containers for storing and protecting an electrophoretic support medium from dehydration and physical damage acknowledged above, the container of the present invention provides a means for securely retaining the support medium within the container by the use of a liquid located between the support medium and the container. In addition, because retention is accomplished by a liquid, moisture is provided within the interior of the container.

The container for an electrophoretic support medium of the present invention includes a top portion and a bottom portion, which when closed sealingly engage with one another. The support medium has a base sheet with at least two opposed major surfaces and a layer of an electrophoretic gel adhered to one of the major surfaces of the base sheet. The bottom portion of the container has a recess formed therein for accommodating the support medium and at least a portion of the recess is a substantially smooth planar surface. A liquid is disposed between the planar surface of the recess of the bottom portion and the other surface of the base sheet. The liquid is in surface contact with the other surface of the base sheet and the planar surface of the recess, whereby the support medium is retained in the recess as a result of the contact adhesion between the liquid and the contacting surfaces.

BRIEF DESCRIPTION OF THE DRAWINGS

The various features, benefits, and advantages of the present invention will become more apparent by reading the following detailed description in conjunction with the drawings where like reference numerals identify corresponding components.

DETAILED DESCRIPTION OF THE PREFERRED EMBODIMENT

Figure 1:
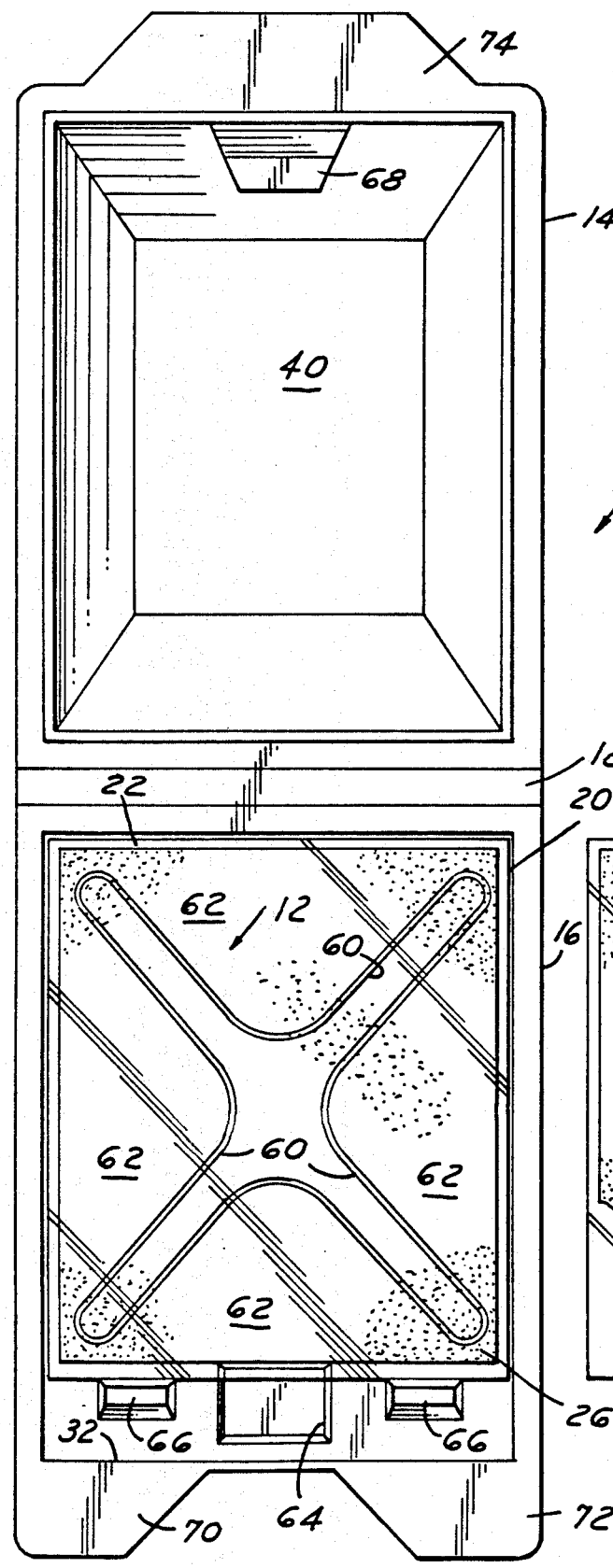
FIG. 1 is a plan view of the container of the present invention, with the container in any opened position and with the electrophoretic support medium retained in the bottom portion thereof.

Referring to FIG. 1 of the drawings, the container of the present invention, generally designated 10, for protecting and enclosing an electrophoretic support medium 12 is illustrated. The container 10 includes a top portion 14 and a bottom portion 16, which when closed sealingly engage with one another. The top portion 14 and the bottom portion 16 are hingedly connected at their edges 18 to permit ease of opening and closing.

Figure 3:
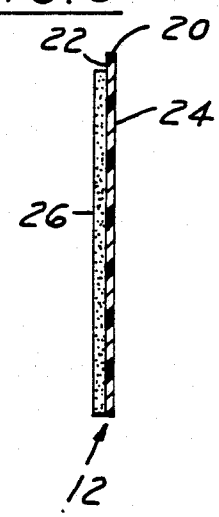
FIG. 3 is a fragmentary cross-sectional view of the electrophoretic support medium illustrating the details of the layer of electrophoretic gel and base sheet taken in the direction of arrows 3—3 of FIG. 2.
Figure 2:
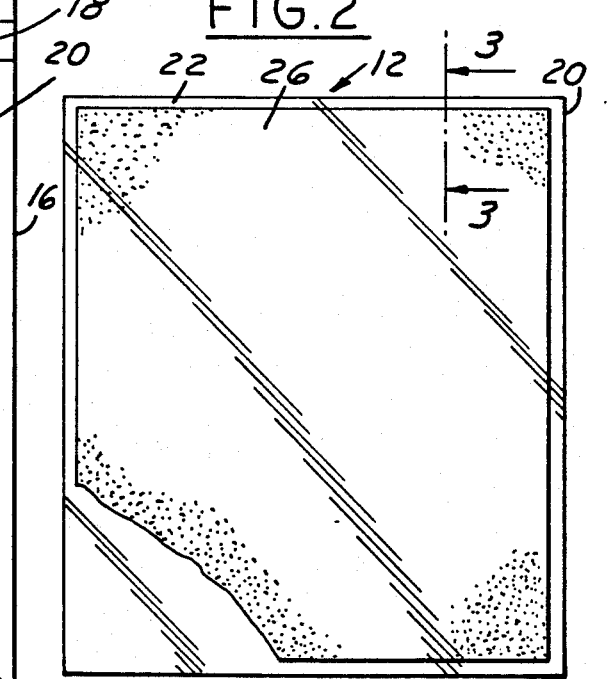
FIG. 2 is a plan view of the electrophoretic support medium with a layer of an electrophoretic gel adhered to a base sheet.

As illustrated in FIG. 2 and in greater detail in FIG. 3, the electrophoretic support medium includes a base sheet 20 which has at least two opposed major surfaces 22 and 24. A layer 26 of an electrophoretic gel is adhered to one of the major surfaces 22 of the base sheet. The particular gel is not essential to the present invention and may include any of the mediums of the prior art mentioned hereinabove. However, agarose has been successfully utilized.

Figure 4:
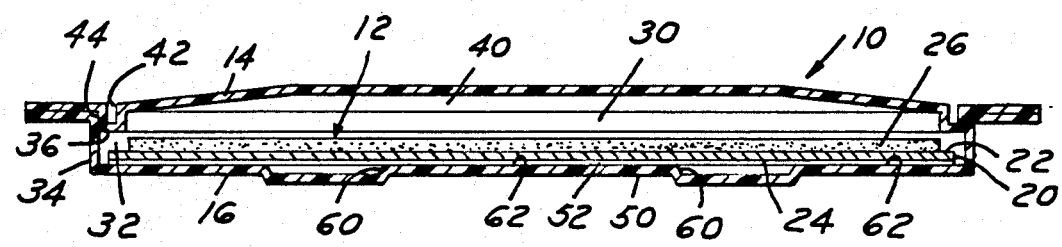
FIG. 4 is an enlarged front cross-sectional view of the container, with the container in a closed position, illustrating retention of the electrophoretic support medium thereby by a liquid placed between the support medium and the container.
Figure 5:
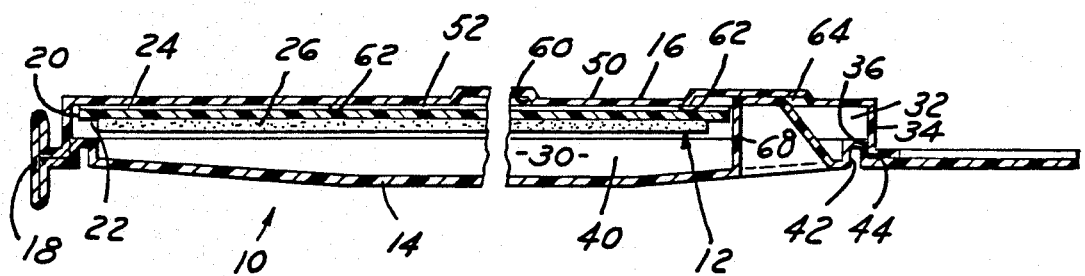
FIG. 5 is an enlarged side fragmentary view of the container, partly in section, with the container in a closed upside down position, illustrating retention of the electrophoretic support medium therein by a liquid placed between the support medium and the container.

When the container 10 is closed by bending the container along edge 18, a cavity 30 is formed within the container by the top portion 14 and the bottom portion 16, as illustrated in FIGS. 4 and 5. The bottom portion 16 includes a recess 32 dimensioned such as to fully contain the support medium 12 therein. Along the edge 34 of the recess is a continuous sealing surface 36. To ensure that the top portion 14 does not come in contact with the gel layer 26, an additional recess 40 is formed in the top portion 14, and a continuous rim 42 protrudes from the top portion 14 into the cavity 30 to further define the recess 40. The rim 42 also includes a continuous sealing surface 44 which contacts the continuous sealing surface 36 of the recess 32 to provide a substantial air-tight cavity when the container is closed. In addition, the rim 42 is spaced apart from the support medium and does not come in contact with the base sheet 20 or the gel layer 26 of the support medium 12.

As illustrated in FIGS. 1, 4 and 5, at least a portion of the recess 32 of the bottom portion 16 includes a substantially smooth planar surface 50. The surface should be substantially smooth to maximize contact between the other or exposed surface 24 of the base sheet 20 and the planar surface 50 of the recess 32. Thus, at least one drop of liquid placed between the planar surface and the base sheet is sufficient to securely retain the support medium 12 within the recess and to prevent it, specifically the gel layer 26, from coming in contact with any part of the container during, for example, shipping and storage. The molecular attraction exerted between the exposed surface 24 of the base sheet 20 and the liquid 52, and the molecular attraction exerted between the planar surface 50 of the recess 32 and the liquid 52 provides the necessary contact adhesion. It is essential that the contact adhesion be sufficient to securely retain the support medium within the recess 32. It has been found that the molecular attraction between the base sheet and the bottom portion is insufficient by itself to securely retain the support medium 12.

Similarly, if the contact adhesion between the liquid molecules an the material of the contacting surfaces is insufficient, a surfactant may be added to the liquid 52 to increase its wetting ability. However, it has been found that when polymeric materials, such as styrene for the container and Mylar for the base sheet ("MYLAR" is a trademark of E. I. DuPont de Nemours & Company of Wilmington, Del.), are utilized contact adhesion is sufficient when a liquid 52, such as water, is placed between them. In addition, the water ensures that sufficient moisture is present within the cavity 30 of the container 10 to limit the rate of dehydration of the gel layer 26. This prolongs its shelf life. Normally, the manufacturers of this product will select the best commercially available material based upon price application and manufacturing process. Also, buffers, preservatives and stabilizers may be added to the liquid separately or in combination for their various purposes. By way of example, AMP or barbital may be utilized as buffers, and sodium azide or thimerosal as preservatives.

As illustrated in FIG. 1, a pair of intersecting valleys 60 are provided in recess 32 to separate the planar surface 50 into four flat plateau portions 62. This substantially reduces air spaces and the like between the contacting surfaces to increase the retention of the support medium 12 within the recess 32.

Further, an additional recess 64 is provided in the recess 32 beneath t he plane of the planar surface 50 so that a person may place his or her finger beneath the base sheet 20 to remove the support medium 12 from the container 10. Such force is sufficient to overcome the contact adhesion present as a result of the liquid. Also, two members 66 protrude from the plane of the planar surface 50 into the recess 32 of the bottom portion 16 for locating the support medium 12 within the recess. Lastly, as illustrated in FIG. 5, a member 68 protrudes from the plane of the recess 40 of the top portion 14, and when the container 10 is closed, the member 68 is accommodated by and comes in contact with the recess 64 to limit the engageability of the top portion 14 and the bottom portion 16 to ensure that the top portion is spaced apart from the support medium 12.

As illustrated in FIGS. 1, to facilitate opening of the container 10, the bottom portion 16 includes a pair of tabs 70 and 72, and the top portion 14 includes a single tab 74. Thus, a person may grasp either of the tabs 70 or 72 of the top portion with one hand, and the tab 74 of the bottom portion 16 with the other hand, and by pulling easily open the container to expose the support medium retained therein.

There are several ways to produce the container 10 of the present invention which are known to those skilled in the art, such as vacuum forming. The particular manufacturing process is not essential to the present invention, and is a matter of choice based upon economics and availability.

While the preferred embodiment of the present invention has been described so as to enable one skilled in the art to practice the techniques of the present invention, the proceeding description is intended to be exemplary and should not be used to limit the scope of the invention. The scope of the invention should be determined only by reference to the following claims.

I claim:

1. A container for protecting and enclosing an electrophoretic support medium having a base sheet with at least two opposed major surfaces and a layer of an electrophoretic gel adhered to one of the major surfaces of the base sheet, comprising:

a top portion and a bottom portion which when closed being sealingly engageable with one another;

said bottom portion having a recess therein for accommodating the support medium, at least a portion of said recess having a substantially smooth planar surface; and a liquid being disposed between the planar surface of said bottom portion and the other surface of said base sheet, said liquid being in surface contact with the other surface of said base sheet and the planar surface of said recess, whereby the support medium may be retained in said recess as a result of the contact adhesion between the other surface of said base sheet and said liquid, and as a result of the contact adhesion between the planar surface of said recess and said liquid.

2. The container defined in claim 1, wherein said liquid includes water.

3. The container defined in claim 2, wherein said water provides moisture to said recess so that the shelf life of said electrophoretic gel is increased by reducing the rate of dehydration of said electrophoretic gel.

4. The container defined in claim 1, wherein said liquid includes a buffer.

5. The container defined in claim 1, wherein said liquid includes a preservative.

6. The container defined in claim 1, wherein said liquid includes a stabilizer.

7. The container defined in claim 1, wherein said liquid includes a surfacant for increasing the wetting ability of said liquid.

8. The container defined in claim 1, wherein the top portion of said container is spaced apart from said recess in which the support medium is located.

9. The container defined in claim 1, wherein said top portion and said bottom portion are hingedly connected to one another to permit the opening and closing of said container.

10. The container defined in claim 1, wherein said top portion and said bottom portion form a cavity therebetween which includes said first mentioned recess, said recess of said bottom portion has a continuous sealing surface; and said top portion has a protruding continuous rim forming a second recess, and said rim having a continuous sealing surface, whereby when said container is closed said rim extends into said recess of said bottom portion and engages the continuous sealing surface of said bottom portion and the protruding rim of said top portion is spaced from said recess and said support medium retained in the recess of said bottom portion.

11. The container defined in claim 1, wherein said recess further comprises at least one valley to separate the planar surface of said recess into at least two flat plateau portions, whereby air spaces between the base sheet of said support medium and the plateau portions of said planar surface are substantially reduced to increase the retention of said base sheet within said recess.

12. The container defined in claim 1, wherein said recess further comprises at least one additional recess situated at least partially beneath said base sheet so that access to the other surface of said base sheet may be gained to permit ease of removal of said base sheet and said layer of electrophoretic gel adhered thereto from said recess.

13. The container defined in claim 12, wherein said top portion further comprises at least one protruding member which when said container is in a closed position is accommodated by said additional recess to limit the engageability of said top portion and said bottom portion and to ensure that said top portion is spaced apart from said support medium.

14. The container defined in claim 1, wherein said planar surface of said bottom portion further comprises locating means protruding into said recess for locating said support medium in said recess.

15. The container defined in claim 1, wherein said container is made of a polymeric material.

16. The container defined in claim 15, wherein the polymeric material is styrene.

17. A container for protecting and enclosing an electrophoretic support medium having a base sheet with at least two opposed major surfaces and a layer of an electrophoretic gel adhered to one of the major surfaces of the base sheet, comprising:
 a top portion and a bottom portion which when closed being sealingly engageable with one another; and
 said bottom portion having a recess dimensioned to accommodate the support medium therein and at least a portion of said recess having a substantially smooth planar surface, so that a liquid solution placed between said planar surface and the other surface of said base sheet may securely retain said support medium within said recess as a result of the contact adhesion between said liquid solution and the contacting surfaces.

18. The container defined in claim 17, wherein said top portion and said bottom portion are hingedly joined along one edge.

* * * * *